United States Patent
Faler et al.

(10) Patent No.: US 10,519,095 B2
(45) Date of Patent: Dec. 31, 2019

(54) SYNTHESIS OF BENZYLANILINYL PHENYL PHENOL LIGANDS

(71) Applicant: Univation Technologies, LLC, Houston, TX (US)

(72) Inventors: Catherine A. Faler, Houston, TX (US); C. Jeff Harlan, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 16/475,807

(22) PCT Filed: Jan. 5, 2018

(86) PCT No.: PCT/US2018/012454
§ 371 (c)(1),
(2) Date: Jul. 3, 2019

(87) PCT Pub. No.: WO2018/129230
PCT Pub. Date: Jul. 12, 2018

(65) Prior Publication Data
US 2019/0352252 A1    Nov. 21, 2019

Related U.S. Application Data

(60) Provisional application No. 62/443,419, filed on Jan. 6, 2017.

(51) Int. Cl.
*C07C 209/22* (2006.01)
*C07C 209/02* (2006.01)

(52) U.S. Cl.
CPC .......... *C07C 209/22* (2013.01); *C07C 209/02* (2013.01)

(58) Field of Classification Search
CPC ........................... C07C 209/22; C07C 209/02
See application file for complete search history.

(56) References Cited

U.S. PATENT DOCUMENTS

2004/0005984 A1    1/2004   Boussie et al.

FOREIGN PATENT DOCUMENTS

WO    2016176138    11/2016

OTHER PUBLICATIONS

International Preliminary Report on Patentability for related PCT Application PCT/US2018/012454, dated Jul. 18, 2019 (7 pgs).
International Search Report & Written Opinion for related PCT Application PCT/US2018/012454, dated Apr. 20, 2018 (13 pgs).
Corey, et al., "Tricyclic Systems which contain Silicon and Nitrogen Heteroatoms in Central Seven- and Eight-Membered Rings"; Journal of Organometallic Chemistry, vol. 194, pp. 15-22 (Jul. 1, 1980).

*Primary Examiner* — Jafar F Parsa
(74) *Attorney, Agent, or Firm* — Brooks, Cameron & Huebsch, PLLC

(57) ABSTRACT

Synthetic methods for the preparation of ligands and metal-ligand complexes are disclosed.

6 Claims, No Drawings

SYNTHESIS OF BENZYLANILINYL PHENYL PHENOL LIGANDS

This application is a National Stage Application under 35 U.S.C. § 371 of International Application Number PCT/US2018/012454, filed Jan. 5, 2018 and published as WO 2018/129230 on Jul. 12, 2018, which claims the benefit to U.S. Provisional Application 62/443,419, filed Jan. 6, 2017, the entire contents of which are incorporated herein by reference in its entirety.

The invention relates to ligands, complexes, and/or catalysts that provide olefin polymerization capabilities.

BACKGROUND OF THE INVENTION

Ligand-metal coordination complexes, e.g., organometallic complexes, are useful as catalysts, additives, stoichiometric reagents, monomers, solid-state precursors, therapeutic reagents and drugs. Complexes of this type ordinarily are prepared by combining a ligand with a suitable metal compound or metal precursor in a suitable solvent at a suitable temperature. The ligand contains functional groups that bind to the metal center(s), remain associated with the metal center(s), and therefore provide an opportunity to modify the steric, electronic and chemical properties of the active metal center(s) of the complex.

Certain ligand-metal complexes are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, dimerization, trimerization, oligomerization, Diels-Alder reactions and other transformations. In the field of polymerization catalysis, in connection with single site catalysis, the ligand typically offers opportunities to modify the electronic and/or steric environment surrounding an active metal center. This allows the ligand to assist in the creation of possibly different polymers. Group 4 metallocene based single site catalysts are generally known for polymerization reactions.

One application for metallocene catalysts is producing isotactic polypropylene. Isotactic polypropylene and its production has been extensively studied. See, e.g., US 2004/0005984 A1.

In view of the industrial importance of this field, it would be desirable to have additional synthetic methods for the preparation of ligands.

SUMMARY OF THE INVENTION

The invention includes a process comprising contacting 2-bromo-N-(2-bromobenzyl)-N-methylaniline with 2-((tetrahydro-2H-pyran-2-yl)oxy)-[1,1'-biphenyl]-3-yl lithium in a polar aprotic reaction medium under reaction conditions, thereby forming 2-(((2'-hydroxy-[1,1':3',1''-terphenyl]-2-yl)(methyl)amino)methyl)-[1,1':3',1''-terphenyl]-2'-ol.

The ligands of the process of the invention are useful in the preparation of catalysts for the polymerization of olefins.

DETAILED DESCRIPTION OF THE INVENTION

As used herein, the terms "a," "an," "the," "at least one," and "one or more" are used interchangeably. The terms "comprises" and "includes" and variations thereof do not have a limiting meaning where these terms appear in the description and claims. Thus, for example, a composition that includes "a" material can be interpreted to mean that the composition includes "one or more" materials.

"Complex" means a coordination compound formed by the union of one or more electronically rich molecules or atoms capable of independent existence with one or more electronically poor molecules or atoms, each of which is also capable of independent existence.

All references to the "Periodic Table of Elements" and the various groups within the Table are to the Table as published in the CRC Handbook of Chemistry and Physics, $71^{st}$ Ed. (1990-1991), CRC Press, at page 1-10.

The term "reaction medium" includes, but is not limited to, a liquid in which at least one reactant is at least partially soluble. Thus, for a given reaction, it is possible that all reactants are solubilized in the reaction medium, but it is also possible that the reactants form a suspension in the reaction medium. Other combinations are also possible.

Unless stated to the contrary, implicit from the context, or customary in the art, all parts and percentages are based on weight and all test methods are current as of the filing date of this disclosure.

The invention includes processes for the preparation of ligands and ligand-metal complexes. For example, one process of the invention comprises the following steps:

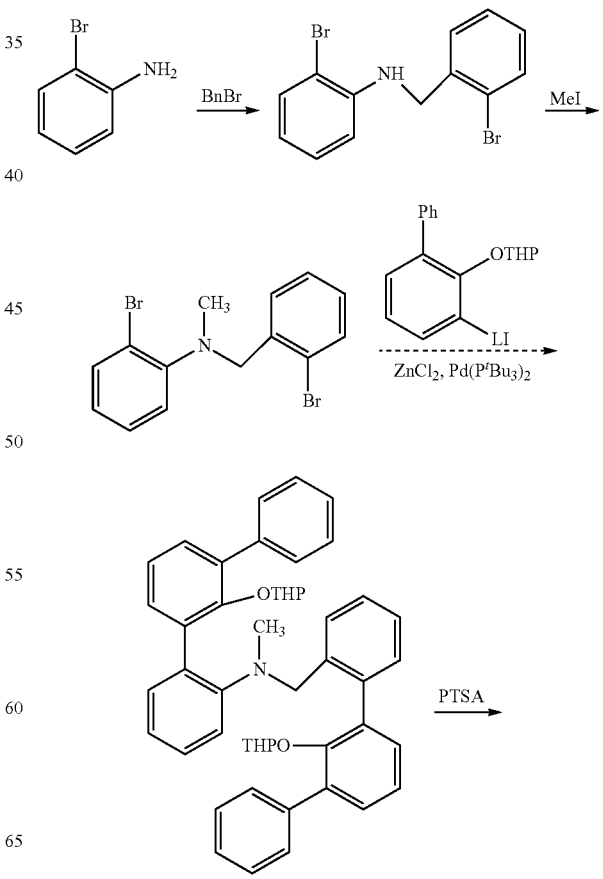

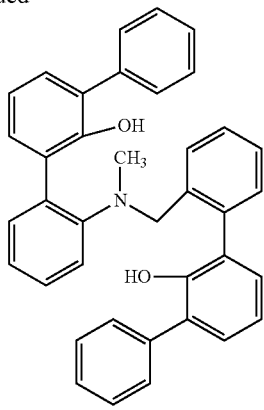

wherein THP" and "THP'" refer to tetrahydropyranyl, Bn is benzyl, MeI is methyl iodide, $^tBu$ refers to tert-butyl and PTSA is para-toluenesulfonic acid.

The process description that follows for the first step of the reaction scheme shown above is one way of performing the reactions of the invention, but one skilled in the art would readily know how to use other reaction conditions (e.g., different temperatures), solvents (e.g., different solvents), and reagents in alternative embodiments to carry out the reactions. For example, in one embodiment of the invention, 2-bromoaniline is reacted with benzyl bromide in a reaction medium to form 2-bromo-N-(2-bromobenzyl) aniline. The reaction may be conducted at a temperature of from 50 to 150° C., preferably from 75 to 125° C. In one embodiment of the invention, in the first step of the reaction scheme shown above, 2-bromoaniline, 2-bromobenzyl bromide, potassium carbonate and tetrabutylammonium iodide are combined in a nonpolar reaction medium, such as toluene, and the mixture is heated at a temperature of from 50 to 150° C. to allow the reaction to proceed to form the product, 2-bromo-N-(2-bromobenzyl)aniline.

The process description that follows for the second step of the reaction scheme shown above is one way of performing the reactions of the invention, but one skilled in the art would readily know how to use other reaction conditions (e.g., different temperatures), solvents (e.g., different solvents), and reagents in alternative embodiments to carry out the reactions. For example, in one embodiment of the invention, 2-bromo-N-(2-bromobenzyl)aniline is contacted with sodium hydride and methyl iodide in a reaction medium to form 2-bromo-N-(2-bromobenzyl)-N-methylaniline. The reaction may be conducted at a temperature of from −50 to 70° C. In one embodiment of the invention, in the second step of the reaction scheme shown above, the product of the first step is dissolved in a polar aprotic solvent, such as dimethylformamide (DMF) and cooled to a temperature of from −50 to 0° C. Sodium hydride is then added in portions and the solution is warmed to a temperature of from 1 to 70° C., preferably ambient temperature, Methyl iodide is then added and the reaction is stirred while allowing the reaction to proceed to form the product 2-bromo-N-(2-bromobenzyl)-N-methylaniline.

The process description that follows for the third step of the reaction scheme shown above is one way of performing the reactions of the invention, but one skilled in the art would readily know how to use other reaction conditions (e.g., different temperatures), solvents (e.g., different solvents), and reagents in alternative embodiments to carry out the reactions. For example, in one embodiment of the invention, 2-bromo-N-(2-bromobenzyl)-N-methylaniline is contacted with 2-((tetrahydro-2H-pyran-2-yl)oxy)-[1,1'-biphenyl]-3-yl lithium and a metal chloride and a metal alkylphosphine in a reaction medium to form the ligand product 2-(((2'-hydroxy-[1,1':3',1"-terphenyl]-2-yl)(methyl) amino)methyl)-[1,1':3',1"-terphenyl)-2'-ol. The reaction may be conducted at a temperature of from 50 to 150° C., preferably from 60 to 100° C. In one embodiment of the invention, in the third step of the reaction scheme shown above, 2-((tetrahydro-2H-pyran-2-yl)oxy)-[1,1'-biphenyl]-3-yl lithium is dissolved in a polar aprotic solvent, such as tetrahydrofuran (THF). Zinc chloride is added and the resulting mixture is allowed to stir before the addition of the product of the second step, followed by the addition of palladium bis(tri-tert-butylphosphine). The resulting brown solution is heated at a temperature of from 50 to 150° C., e.g. 75° C., to allow the reaction to proceed and to form the ligand product 2-(((2'-hydroxy-[1,1':3',1"-terphenyl]-2-yl) (methyl)amino)methyl)-[1,1':3',1"-terphenyl)-2'-ol. The reaction mixture is then quenched.

A ligand metal complex may be formed in a subsequent step if desired.

The catalysts in some embodiments are compositions comprising the ligand and metal precursor, and optionally may additionally include an activator, combination of activators or activator package. In other embodiments, the catalysts are metal-ligand complexes and optionally may additionally include an activator, combination of activators or activator package.

The ligands that are suitable for use in the catalysts herein have several general, alternative descriptions. In one embodiment, the ligands are dianionic, chelating ligands that may occupy up to four coordination sites of a metal atom. The ligands can also be described as dianionic ligands that, when chelated to a metal atom, form at least one or two metalocycles (counting the metal atom as one member of the ring). Also, in some embodiments, the ligands can be described as dianionic, chelating ligands that use either oxygen or sulfur as binding atoms to the metal atom. In still other embodiments, the ligands can be described as non-metallocene ligands that can coordinate in an approximate $C_2$-symmetrical complex with a metal atom. These embodiments can be used together or separately.

It is required that there be at least 2 hydrogen atoms associated with each ligand that are capable of being removed in a complexation reaction with a metal atom or metal precursor or base. In some embodiments, prior to such a complexation reaction, a base may be reacted with the ligand to form a salt, the product of which may then be reacted with a metal precursor ML, wherein M is a metal selected from the group consisting of groups 3-6 and Lanthanide elements of the Periodic Table of Elements, preferably from group 4 (Hf, Zr and Ti); and L is independently selected from the group consisting of halide (F, Cl, Br, I).

Ligands within the scope of this invention may be prepared according to the general scheme shown above, where building blocks are first prepared and then coupled together with the proviso that similar schemes may be used to prepare ligands other than the ligand shown herein.

In general, building blocks are prepared that are then linked together with a bridging group. Variations in the aromatic ring substituents can be introduced in the synthesis of the building blocks. Variations in the bridge can be introduced with the synthesis of the bridging group.

Once the desired ligand is formed, it may be combined with a metal atom, ion, compound or other metal precursor compound, e.g. ML, wherein M and L are as defined above.

In some applications, the ligands of this invention will be combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

Activators and their use are well-known to those skilled in the art. Broadly speaking, the activator may comprise alumoxanes, Lewis acids, Bronsted acids, compatible non-interfering activators and combinations of the foregoing. These types of activators have been taught for use with different compositions or metal complexes in the following references, which are hereby incorporated by reference in their entirety: U.S. Pat. Nos. 5,599,761, 5,616,664, 5,453,410, 5,153,157, and 5,064,802. In particular, ionic or ion forming activators are preferred.

The ligands, complexes or catalysts may be supported on organic or inorganic supports. Suitable supports include silicas, aluminas, clays, zeolites, magnesium chloride, and polymeric supports such as polystyrenes, substituted polystyrenes and the like. Polymeric supports may be cross-linked or not. In addition, the catalysts of this invention may be combined with other catalysts in a single reactor and/or employed in a series of reactors (parallel or serial) in order to form blends of polymer products.

The ligands, complexes and/or catalysts are particularly effective at polymerizing α-olefins (such as propylene, 1-butene, 1-pentene, 1-hexene, 1-heptene, 1-octene, and styrene), copolymerizing ethylene with α-olefins (such as propylene, 1-butene, 1-pentene, 1-hexene, 1-heptene, 1-octene, and styrene), and copolymerizing ethylene with 1,1-disubstituted olefins (such as isobutylene). These compositions might also polymerize monomers that have polar functionalities in homopolymerizations or copolymerizations and/or homopolymerize 1,1- and 1,2-disubstituted olefins. Also, diolefins in combination with ethylene and/or α-olefins or 1,1- and 1,2-disubstituted olefins may be copolymerized. Methods for polymerizing these monomers are well-known to those skilled in the art. The ligands, metal-ligand complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. Methods of conducting combinatorial chemistry are well-known to those skilled in the art.

Specific Embodiments of the Invention

General: All reagents are purchased from commercial vendors and used as received unless otherwise noted. Solvents are sparged with $N_2$ and dried over 3 Å molecular sieves. Analytical thin-layer chromatography (TLC) is performed on Selecto Plates (200 μm) precoated with a fluorescent indicator. Visualization is effected using ultraviolet light (254 nm). Flash column chromatography is carried out with Sigma Aldrich Silica gel 60 Å (70-230 mesh) using solvent systems specified. NMR spectra are recorded on a Bruker 400 and/or 500 NMR with chemical shifts referenced to residual solvent peaks.

Example 1—Preparation of
2-bromo-N-(2-bromobenzyl)aniline (509-23)

2-bromoaniline (5.0 g, 29 mmol), 2-bromobenzyl bromide (7.2 g, 29 mmol), potassium carbonate (8.0 g, 58 mmol), and tetrabutylammonium iodide (TBAI) (approx. 100 mg) are combined in 50 mL of toluene and heated at 100° C. overnight. The mixture is then cooled, filtered and concentrated giving the product as a pale yellow oil which solidifies upon standing: Rf=0.67 (10:90 acetone:hexane); $^1$H NMR (400 MHz, $CDCl_3$, δ): 4.50 (d, J=6.4 Hz, 2H), 4.94 (br s, 1H), 6.60 (m, 2H), 7.16 (m, 2H), 7.28 (m, 1H), 7.36 (m, 1H), 7.47 (m, 1H), 7.61 (m, 1H); $^{13}$C NMR (125 MHz, $CDCl_3$, δ): 46.3, 110.0, 111.9, 118.4, 123.4, 127.8, 128.7, 128.9, 129.0, 132.7, 133.1, 137.7, 144.6.

Example 2—Preparation of 2-bromo-N-(2-bromobenzyl)-N-methylaniline (509-33)

The benzylaniline 509-23 (4.0 g, 11.7 mmol) of Ex. 1 is dissolved in 30 mL of dimethylformamide (DMF) and cooled to −35° C. Sodium hydride (442 mg, 23.4 mmol) is added in portions and the solution is warmed to ambient temperature over 30 min. Methyl iodide (1.45 mL, 23.4 mmol) is then added and the reaction stirred overnight before quenching with saturated ammonium chloride. The mixture is extracted with ether and ethyl acetate, and the combined organic layers are washed twice with water and twice with brine. It is then dried (MgSO4), filtered, and concentrated under reduced pressure. The resulting oil is purified by silica gel chromatography using 20% acetone/isohexane as an eluent. The product is obtained as a yellow solid in 88% yield from aniline: Rf=0.51 (20:80 acetone:hexane); $^1$H NMR (500 MHz, $CDCl_3$, δ): 2.76 (s, 3H), 4.30 (s, 2H), 6.91 (m, 1H), 7.14 (m, 2H), 7.29 (m, 2H), 7.59 (m, 2H), 7.75 (d, J=7.65 Hz, 1H); $^{13}$C NMR (125 MHz, $CDCl_3$, δ): 41.2, 60.0, 120.2, 122.3, 123.9, 124.5, 127.6, 128.3, 128.6, 130.3, 132.7, 134.2, 137.6, 151.3.

Example 3—Preparation of 2-(((2'-hydroxy-[1,1':3',1''-terphenyl]-2-yl)(methyl)amino)methyl)-[1,1':3',1''-terphenyl)-2'-ol (209-44)

2-((tetrahydro-2H-pyran-2-yl)oxy)-[1,1'-biphenyl]-3-yl lithium (3.3 g, 10.0 mmol) is dissolved in 30 mL of THF. Zinc chloride (1.3 g, 10.0 mmol) is added and the resulting mixture is allowed to stir for approximately 5 min before the addition of the dibromo compound 509-33 (1.7 g, 5.0 mmol) of Ex. 2, and then by the addition of palladium bis(tritert-butylphosphine) (75 mg, 0.14 mmol). The resulting brown solution is heated at 75° C. for 1.5 h. The reaction is quenched with saturated ammonium chloride and is extracted with 3 portions of ethyl acetate. The combined organic layers are dried (MgSO4), filtered, and concentrated under reduced pressure. The resulting oil is dissolved in 40 mL of methanol/THF with approx. 100 mg of p-toluenesulfonic acid and is stirred overnight. Upon concentration, the crude product is loaded onto a silica gel column and is eluted with 20% acetone/isohexane to give the product as a white solid: $^1$H NMR (400 MHz, $CDCl_3$, δ): 2.4 (s, 3H), 3.70 (d, J=14 Hz, 1H), 3.86 (d, J=14 Hz, 1H), 4.82 (s, 1H), 6.89 (m, 4H), 7.16 (m, 11H), 7.36 (m, 7H), 7.53 (m, 2H), 10.22 (s, 1H); $^{13}$C NMR (125 MHz, $CDCl_3$, δ): 38.7, 58.1, 119.98, 120.8, 121.0, 124.9, 127.0-132.0 (23C), 134.1, 134.6, 135.2, 137.6 (2C), 148.4, 149.5, 151.9.

What is claimed is:

1. A process comprising contacting 2-bromo-N-(2-bromobenzyl)-N-methylaniline with 2-((tetrahydro-2H-pyran-2-yl)oxy)-[1,1'-biphenyl]-3-yl lithium in a polar aprotic reaction medium under reaction conditions, thereby forming 2-(((2'-hydroxy-[1,1':3',1''-terphenyl]-2-yl)(methyl)amino)methyl)-[1,1':3',1''-terphenyl]-2'-ol.

2. The process of claim 1 further comprising a preliminary step to prepare the 2-bromo-N-(2-bromobenzyl)-N-methylaniline, wherein the preliminary step comprises contacting 2-bromo-N-(2-bromobenzyl)aniline with methyl iodide in a reaction medium under reaction conditions, thereby forming the 2-bromo-N-(2-bromobenzyl)-N-methylaniline.

3. The process of claim 2 further comprising a second preliminary step to prepare the 2-bromo-N-(2-bromobenzyl)aniline, wherein the second preliminary step comprises contacting 2-bromobenzyl bromide with 2-bromoaniline in a reaction medium under reaction conditions, thereby forming the 2-bromo-N-(2-bromobenzyl)aniline.

4. The process of claim 1 wherein the contacting further comprises contacting the 2-bromo-N-(2-bromobenzyl)-N-methylaniline, 2-((tetrahydro-2H-pyran-2-yl)oxy)-[1,1'-biphenyl]-3-yl lithium, and reaction medium with zinc chloride and palladium bis(tri-tert-butylphosphine).

5. The process of claim 2 wherein the contacting of the preliminary step further comprises contacting the 2-bromo-N-(2-bromobenzyl)aniline, methyl iodide and reaction medium with sodium hydride.

6. The process of claim 3 wherein the contacting of the second preliminary step further comprises contacting the 2-bromobenzyl bromide, 2-bromoaniline, and reaction medium with potassium carbonate and tetrabutylammonium iodide.

* * * * *